(12) United States Patent
Agholme

(10) Patent No.: US 6,503,946 B1
(45) Date of Patent: Jan. 7, 2003

(54) PREPARATION FOR WARTS

(76) Inventor: Astrid Agholme, Rosendalsvägen 4, SE-776 31 Hedemora (SE)

( * ) Notice: Subject to any disclaimer, the term of this patent is extended or adjusted under 35 U.S.C. 154(b) by 0 days.

(21) Appl. No.: 09/889,740

(22) PCT Filed: Jan. 18, 2000

(86) PCT No.: PCT/SE00/00088

§ 371 (c)(1), (2), (4) Date: Aug. 15, 2001

(87) PCT Pub. No.: WO00/45808

PCT Pub. Date: Aug. 10, 2000

(30) Foreign Application Priority Data

Jan. 21, 1999 (SE) .............................................. 9900177

(51) Int. Cl.⁷ .............................................. A61K 31/19
(52) U.S. Cl. ....................................................... 514/557
(58) Field of Search ......................................... 514/557

(56) References Cited

FOREIGN PATENT DOCUMENTS

| | | |
|---|---|---|
| EP | 0 259 617 A2 | 8/1987 |
| EP | 0 527 241 A1 | 7/1991 |
| EP | 0 913 150 A1 | 8/1998 |
| WO | WO 98/17288 A1 | 4/1998 |

OTHER PUBLICATIONS

STN International, File BIOSIS, Biosis Accession No. 1987:233440, Document No. BA83:121610, Tsankov N. et al.: "Method of the Treatment of Condyloma Acuminata" Dermatol Venerol, 1986 (RECD 1987) 25(4), 67–69.

*Primary Examiner*—Raymond Henley, III
(74) *Attorney, Agent, or Firm*—Burns, Doane, Swecker & Mathis, LLP

(57) ABSTRACT

Use of a preparation comprising formic acid as an active ingredient for the manufacture of a medicament for the treatment of skin warts caused by a papilloma virus in a mammal by topical administration on the affected area.

8 Claims, No Drawings

PREPARATION FOR WARTS

This is a 371 of PCT/SE00/00088 filed Jan. 18, 2000.

TECHNICAL FIELD OF THE INVENTION

The present invention relates to the use of a preparation comprising formic acid as an active ingredient for the manufacture of a medicament for the treatment of warts caused by virus(es) in a mammal, especially a human being, by topical administration of the medicament on the affected area.

TECHNICAL BACKGROUND

Warts (verucca) are harmless growths of the skin caused by a wart virus, a so called papilloma virus. This virus can be found in both human beings and animals and constitutes a sub-group to the papova virus family. There are about 60 types of said virus in human beings.

Warts are common affections among human beings and are contagious and can propagate to different parts of the body and among persons. They can grow on any part of the body, but mainly on hands and feet. Warts on hands are often high, cracked and uneven, so called cauliflower warts, on the surfaces of which small black dots can be observed. Said black dots are small capillaries which can easily start bleeding when the wart is being touched, leading to a high risk of infection. On the feet there are among others so called inwards directed warts, which are hard and usually existing on the sole and heel. These warts are the most painful and difficult to treat and easily propagate to form a whole family. On the hands there are also smaller warts, so called ball warts, which are small, deep and considerably more difficult to eliminate. Smaller warts can also be found under the nails.

There is today no effective treatment of warts due to the inability to kill the virus. The treatments, which presently exist, aim at destroying the outer layer of the skin on which the wart is growing. This can be both painful and unpleasant for the patient in question. The chemical preparations for warts available today (in pharmacies) for this treatment contain, among other things, lactic acid, salicylic acid and ether in different concentrations and are strongly corrosive. The skin will be very strongly challenged by this application, which shall be made daily, and inflammations will often be the result. After the application of the preparation for warts on the warts the preparation has to dry, in order to achieve any effect. The film of preparation for warts formed after drying is easily removed for example at contact with water. In addition thereof, the warts seldom disappear by these chemical agents and the warts often reappear. It has been found that, after removal of the outer layer of skin where the wart is situated, it is not certain that the wart has been eliminated. The root of the wart is some layers of skin further under that skin which has been removed. Further chemical treatment is required which by now is very painful and can bring about infections and risks for the wart to recur and the virus to remain.

Another common method of treatment presently used is cryo treatment of the warts with liquid nitrogen. The warts and the surrounding skin are exposed to the treatment, resulting in formation of blisters which resemble burns. The wart is removed after drying of the blister. This treatment is usually very painful and sensitive patients have to be medicated with analgesics.

Another method of treatment for treating warts, which is used especially by foot specialists and skin therapists is the freezing pistol. The pistol is used at such a low temperature as —90° C. and can be painful. Besides, it is necessary to repeat the treatment five to ten times with a fortnight's interval. After the treatment the wart has to be covered with a special plaster for two weeks for the wart to be choked. The plaster is not allowed to come off at contact with water. The pistol and the equipment therefor is expensive, resulting in difficulties for foot specialists to make this activity profitable.

Other methods of treatment comprise operation and the use of laser. These methods are long lasting and complicated. Besides, they often lead to the result that the patient has to report sick.

A further method of treatment, which is presently used for the treatment of warts is the use of special plasters which are placed over the area of warts. However, to achieve any effect of these plasters they have to be changed rather often. Besides, it is not to be recommended to stay in water during this method of treatment as the plasters then easily come off and thus no effect is achieved.

SUMMARY OF THE INVENTION

The object of the present invention is to accomplish a solution to the problems described above by providing an improved preparation of warts. According to the invention this object is achieved by the use of a preparation comprising formic acid as an active ingredient for the manufacture of a medicament for the treatment of skin warts caused by a papilloma virus in a mammal, especially a human being, by topical administration of the medicament to the affected area.

The preparation according to the present invention is used as a medicament for the treatment of warts on the skin in such a way that an effect is achieved by the preparation on the area of warts during 4–5 days after the first application of the preparation. The preparation of formic acid is quickly absorbed into the skin. Initially the warts will become somewhat larger and the blood capillaries will appear distinctly. Either the whole wart will be removed including the root within a short time or further treatment will be needed. Further treatment will depend on the nature, type, sort, age of the wart and the number of warts and on the patient being treated. As the preparation of formic acid is absorbed very quickly into the skin the patient can, without problems, stay in water directly after the treatment. This will not influence on the outcome of the treatment and further preparation of formic acid for application on the area of warts is not necessary.

To achieve the best possible effect the treatment should be repeated once or several times with one week's interval if required. The patient can treat himself, which makes the method both quick and easy.

The expression "preparation comprising formic acid as an active ingredient" as used herein is intended to comprise in addition to formic acid, also derivatives of formic acid, for example esters or salts thereof, which in connection with the treatment form the active ingredient.

According to one aspect of the present invention the formic acid is used within a concentration range of 40–90% by weight, preferably within the range 40–85% by weight, most preferably a concentration of about 85% by weight. The concentration of formic acid used, depends on the nature of the wart, for example depending on the wart being a cauliflower wart, an inwards directed foot wart or a ball wart, the number of warts and on the patient, for example if the person being treated is a grown up or a child. The concentration of the formic acid used in the preparation according to the present invention should thus be chosen in such a way that the concentration is well adapted to the specific area of warts and to the part of the body where the area of warts is situated.

According to a further aspect of the present invention pharmaceutically acceptable carriers, such as water, oil, glycerol, alcohol or mixtures thereof can be comprised in the preparation of formic acid to achieve a softening effect around the area of warts.

The preparation of formic acid according to the present invention can be used for treating all kinds of skin warts caused by papilloma virus (es), preferably on feet and hands.

The use of a preparation comprising formic acid as an active ingredient for the manufacture of a medicament for the treatment of warts caused by a virus according to the present invention will bring about healing to 100% without any scar formation, with quick healing from beneath, after a short time of treatment. Thus, the preparation according to the present invention is very effective for the treatment of warts. Besides, it is essentially free from pain, making the preparation easy to use on children.

The preparation of formic acid acts on the virus in such a manner that the small blood capillaries in the wart will grow together to one single capillary, which thus corresponds to one single root, which can then, after a sufficient treatment, easily be removed.

The skilled man realises how the effect of the treatment can be maximised. Thus, the preparation according to the present invention can be comprised in each of the following forms of coating: ointments, lotions, suspensions, gels, sprays or in other topical carriers suitable for the treatment, whereby in this context conventional carriers and optional additives are used.

The preparation of formic acid according to the present invention enables foot specialists and therapists as well as patients in an effective manner to, cheaply and essentially without pain, remove warts without infections.

The invention will be further illustrated below by specific examples, which are not in any way intended to limit the scope of protection of the invention.

DETAILED DESCRIPTION OF PREFERRED EMBODIMENTS

To obtain the best result the wart should be softened with hot water and hard skin covering the wart should if necessary be scraped off. If the wart is an open or cracked wart, a so called cauliflower wart, it is sufficient to simply wash the wart with water. Take a drop of the wart preparation or use a cotton pad stick (Topzy) to apply the preparation of warts on the area of wart. The preparation is directly absorbed and has an effect for 4–5 days. The procedure should be repeated until the warts have been eliminated. The number of treatments demanded varies depending on the nature of the wart, the number of warts, how long the wart has existed and on the patient being treated.

To illustrate the efficiency of the preparation comprising formic acid as an active ingredient according to the present invention said preparation has been tested on persons with warts, which have earlier been treated by chemical preparations from the pharmacy or with a freezing pistol. However, it has not been possible to remove the warts in question with the formerly used methods.

TABLE 1

| Patient | Location of wart | Number of warts on the patient | Time of existence of the warts in question (month) | Result: number of treatments for removal of the warts |
|---|---|---|---|---|
| 1 | Hand | 1 | 12 | 3 |
| 2 |  | 6 | 12 | 2 |
| 3 |  | 15 | 12 | 4 |
| 4 |  | 20 | 12 | 10 |
| 5 |  | 1 | 60 | 6 |
| 6 | Foot | 27 | 36 | 7 |
| 7 |  | 5 | 12 | 3 |
| 8 |  | 12 | 12 | 4 |
| 9 |  | 1 | 6 | 3 |
| 10 |  | 50 | 36 | 10 |
| 11 |  | 1 | 36 | 6 |
| 12 |  | 2 | 24 | 6 |
| 13 |  | 10 | 10 | 8 |
| 14 |  | 1 | 12 | 3 |
| 15 |  | 4 | 60 | 7 |

The conclusion that can be drawn from the results given above is that the warts are removed after the treatment with the preparation according to the invention. The number of treatments required depend on the number of warts, the nature of the wart, how long the wart(s) has(have) existed and on the patient.

What is claimed is:

1. A method for the treatment of skin warts caused by papilloma virus comprising topically applying to the affected area an effective amount of formic acid to a patient in need of such treatment.

2. The method according to claim 1, wherein the warts are treated on the hands or feet.

3. The method according to claim 1, wherein the formic acid is topically applied along with a pharmaceutically acceptable carrier.

4. The method according to claim 3, wherein the formic acid comprises 40 to 90% by weight of the topical application.

5. The method according to claim 4, wherein the formic acid comprises 40 to 85% by weight of the topical application.

6. The method according to claim 5, wherein the formic acid comprises 85% by weight of the topical application.

7. The method according to claim 1, wherein the pharmaceutically acceptable carrier is selected from the group consisting of water, glycerol, oil, alcohol and mixtures thereof.

8. The method according to claim 1, wherein the patient is a human being.

* * * * *